United States Patent
Abbey et al.

(10) Patent No.: US 6,340,731 B1
(45) Date of Patent: Jan. 22, 2002

(54) POLYCARBOMETALLANE

(75) Inventors: Kirk J. Abbey, Raleigh, NC (US); Fernando J. Gomez; Kenneth B. Wagener, both of Gainesville, FL (US)

(73) Assignee: Lord Corporation, Cary, NC (US)

( * ) Notice: Subject to any disclaimer, the term of this patent is extended or adjusted under 35 U.S.C. 154(b) by 0 days.

(21) Appl. No.: 09/298,288

(22) Filed: Apr. 23, 1999

Related U.S. Application Data

(60) Provisional application No. 60/082,963, filed on Apr. 24, 1998.

(51) Int. Cl.$^7$ ................................................. C08F 30/04
(52) U.S. Cl. ................. 526/241; 526/348.2; 526/348.5; 526/348.6; 526/240
(58) Field of Search ........................... 526/348.6, 348.2, 526/348.5, 240, 241, 901, 902

(56) References Cited

U.S. PATENT DOCUMENTS

| | | |
|---|---|---|
| 3,314,980 A | 4/1967 | Rudner et al. |
| 5,110,885 A | 5/1992 | Wagener et al. |
| 5,290,895 A | 3/1994 | Wagener et al. |
| 5,488,091 A | 1/1996 | Tilley et al. |
| 5,717,051 A | 2/1998 | Hiraoka et al. |
| 5,847,064 A | * 12/1998 | Wagener et al. ............ 526/335 |
| 5,858,541 A | 1/1999 | Hiraoka et al. |

OTHER PUBLICATIONS

Gomez, F.J.; Wagener, K.B. "Polymetallane Segments in ADMET Polymers" *Polym. Prepr.* (*Am. Chem. Soc., Div. Polym. Chem.*)1998, 39(1), 540.

Shibata, K.; Weinert, C.S.; Sita, L.R. "Deconvoluting Steric and Electronic Substituent Effects On the Properties of Linear Oligostannanes: Syntehsis and Characterization of a New Series Incorporating the Bu$^{1,2}$Sn Group" *Organometallics* 1998, 17, 2241.

Braunstein, P.; Mmorise, X. "Reactivity of Heterobimetallic Alkoxysilyl and Siloxy Complexes in the Catalytic Dehydrogenative Coupling of Tin Hydrides" *Organometallics* 1998, 17, 450.

Imori, T. et al. "Metal–Catalyzed Dehydropolymerization of Secondary Stannanes to High Molecular Weight Polystannanes" *J. Am. Chem. Soc.* 1995, 117, 9931.

Kawakami, T. et al. "Highly Coordinated Thin Hydrides: A Novel Synthesis of Tertieray Amines Via Hydrostannation of Imines" *J. Org. Chem.* 1995, 60, 2677.

Sita, L.R. "A New Strategy for the Syntehsis of Homologously Pure Linear Polystannane Oligomers" *Organometallics* 1992, 11, 1442.

Jousseaume, B.; Chanson, E. "Mild Selective Deoxygenatio of Amine Oxides by Tin–Tin Bonded Derivatives" *Synthesis* 1987, 55.

Neumann, W.P.; Pedain, J. "Synthesen mit Organo–Halogenozinn–Hydriden" *Tetrahedron Lett.* 1964, (36), 2461.

Wolf, Patrick S.; Gomez, Fernando J.; Wagener, Kenneth B. "Metal–Containing Polymers Synthesized via Acyclic Diene Metathesis: Polycarbostannanes" *Macromolecules* 1997, 30, 714–717.

Gomez et al., Polymer Preprint, ACS, Division of Polymer Chemistry, 1998, 39(1), p. 540.*

Imori et al. (JACS, vol. 117, No. 40, Oct. 11, 1995, p. 9933).*

* cited by examiner

*Primary Examiner*—David W. Wu
*Assistant Examiner*—William K Cheung
(74) *Attorney, Agent, or Firm*—Miles B. Dearth

(57) ABSTRACT

A polymer having a backbone repeat unit that includes at least two metal atoms bonded to each other and only one ethylenically unsaturated functional group wherein the backbone unit preferably has a structure of

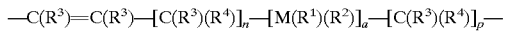

wherein n is 0 to 4; a is at least 2; p is 0 to 4; $R^1$ and $R^2$ are each independently selected from hydrogen, halogen, lower alkyl having 4 or fewer carbon atoms, alkenyl having 4 or fewer carbon atoms, or aromatic having one ring; $R^3$ and $R^4$ are each independently selected from hydrogen and lower alkyl having 1 to 4 carbon atoms; and M is a metal atom selected from at least one of Sn, Ge, Pb, Hg, Ni, Pd, Pt, Cr, Fe, Co, Cu and Zn.

The polymer has at least 20 weight percent metal, preferably at least 50 weight percent metal, based on the weight of the polymer.

10 Claims, No Drawings

POLYCARBOMETALLANE

This application claims benefit of U.S. Provisional Patent Application No. 60/082,963 filed Apr. 24, 1998.

BACKGROUND OF THE INVENTION

Acyclic diene metathesis (ADMET) polymerization is a step polycondensation process that has been used to obtain macromolecules. In ADMET polymerization, a diene is efficiently condensed to an unsaturated polymer by the removal of a small olefin (usually ethylene).

SUMMARY OF THE INVENTION

There is provided according to the present invention a polymer having an ethylenically unsaturated backbone repeat unit that includes at least two metal atoms bonded to each other wherein the backbone repeat unit includes only one ethylenically unsaturated functional group or the ethylenically unsaturation is separated by at least one saturated carbon atom from the metal-to-metal atoms. Preferably, the polymer includes a backbone repeat unit having the formula:

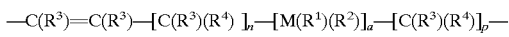

wherein n is 0 to 4 or 0 to 50, preferably 2 to 50; a is at least 2; p is 0 to 4 or 0 to 50, preferably 2 to 50; $R^1$ and $R^2$ are each independently selected from hydrogen, halogen, lower alkyl having 4 or fewer carbon atoms, alkenyl having 4 or fewer carbon atoms, or aromatic having one ring; $R^3$ and $R^4$ are each independently selected from hydrogen and lower alkyl having 1 to 4 carbon atoms; and M is a metal atom selected from at least one of Sn, Ge, Pb, Hg, Ni, Pd, Pt, Cr, Fe, Co, Cu and Zn.

The present invention also provides a method for making an ethylenically unsaturated polymer that includes at least two metal atoms bonded to each other comprising reacting a diene monomer that includes a polymetallane segment in the presence of an effective catalyst to obtain the polymer.

In particular, the polymers of the invention (III) are synthesized via acyclic diene metathesis (ADMET) polymerization of telechelic polymetallane dienes (I) catalyzed by olefin metathesis catalysts based on organometallic complexes of transition metals such as Mo, W, Ta, Ti, Ru (II), Re, Os or Nb.

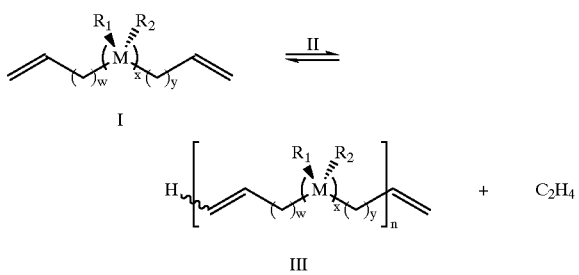

There are numerous known metathesis catalysts that might be useful in the invention. Transition metal carbene catalysts are well known. Illustrative metathesis catalyst systems include rhenium compounds (such as $Re_2O_7/Al_2O_3$, $ReCl_5/Al_2O_3$, $Re_2O_7/Sn(CH_3)_4$, and $CH_3ReO_3/Al_2O_3$—$SiO_2$); ruthenium compounds (such as $RuCl_3$, $RuCl_3$ (hydrate), $K_2[RuCl_5$—$H_2O]$,$[Ru(H_2O)_6](tos)_3$("tos" signifies tosylate), ruthenium/olefin systems (meaning a solution or dispersion of preformed complex between Ru and olefin (monomer) that also includes a β-oxygen in the presence or absence of a soluble or dispersed polymer where the polymer can be an oligomer or higher molecular weight polymer prepared by metathesis or other conventional polymerization synthesis), and ruthenium carbene complexes as described in detail below); osmium compounds (such as $OsCl_3$, $OsCl_3$(hydrate) and osmium carbene complexes as described in detail below); molybdenum compounds (such as molybdenum carbene complexes (such as t-butoxy and hexafluoro-t-butoxy systems), molybdenum pentachloride, molybdenum oxytrichloride, tridodecylammonium molybdate, methyltricaprylammonium molybdate, tri (tridecyl)ammonium molybdate, and trioctylammonium molybdate); tungsten compounds (such as tungsten carbene complexes (such as t-butoxy and hexafluoro-t-butoxy systems), $WCl_6$ (typically with a co-catalyst such as $SnR_4$ (R signifies alkyl) or $PbR_4$), tungsten oxytetrachloride, tungsten oxide tridodecylammonium tungstate, methyltricaprylammonium tungstate, tri(tridecyl)ammonium tungstate, trioctylammonium tungstate, $WCl_6/CH_3CH_2OH/CH_3CH_2AlCl_2$, $WO_3/SiO_2/Al_2O_3$, $WCl_6/2,6$—$C_6H_5$—$C_6H_5OH/SnR_4WCl_6/2,6$-Br—$C_6H_3OH/SnR_4$, $WOCl_4/2,6$-$C_6H_5$—$OH/SnR_4$, $WOCl_4/2,6$-Br—$C_6H_3OH/SnR_4$); $TiCl_4/$ aluminum alkyl; $NbO_x/SiO_2$/iso-butyl $AlCl_2$; and $MgCl_2$. As indicated above, some of these catalysts, particularly tungsten, require the presence of additional activator or initiator systems such as aluminum, zinc, lead or tin alkyl. Preferred catalysts are ruthenium compounds, molybdenum compounds and osmium compounds.

Telechelic polymetallane dienes (I) may be synthesized using any single or a combination of the following procedures according to the invention:

1) The use of alkenyl metallanes (IV) as chain limiters in the dehydrogenation of metal dihydrides (V) catalyzed by organometallic complexes of transition metals such as Zr, Ti, Rh, Pt, Pd, Ni, V, Hf, Sc or Ta (VI).

Scheme A

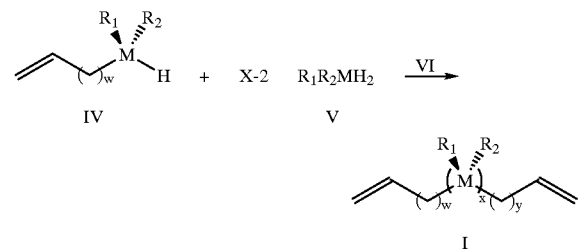

2) The use of alkenyl metal halides (VII) as chain limiters in the Wurtz-type coupling of metal dihalides (VIII) in the presence of alkali metals such as Li, Na, K, Rb or Cs (IX).

Scheme B

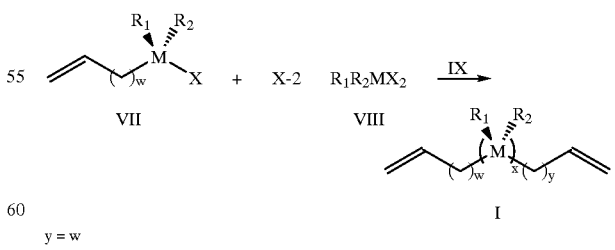

3) The sequential alkenylation of polymetallane dihalides (XI) by organometallic reagents bearing the alkenyl moiety (X) (w and y are independently any number between 2 and 50).

Scheme C

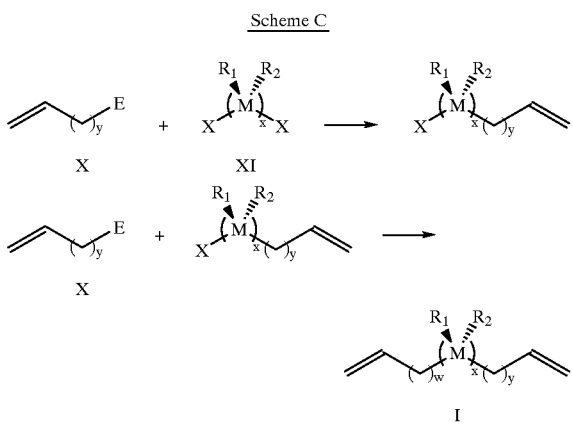

The coupling of alkenyl metallanes (IV) with metal diamides (XII).

Scheme D

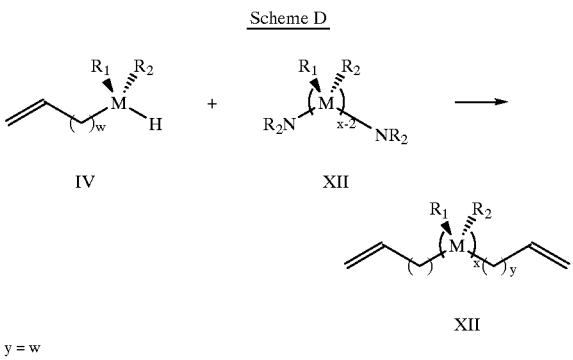

y = w

In all schemes:
M is a metal atom selected from at least one of Sn, Ge, Pb, Hg, Ni, Pd, Pt, Cr, Fe, Co, Cu and Zn;
$R_1$ and $R_2$ are independently hydrogen, alkyl or aryl groups containing 2 to 50 carbons;
w and y are independently any number between 2 and 50;
x and n are independently any number larger than 1;
X is a halogen atom such as Cl, Br or I;
E is any electrophile consisting of or containing metals such as Li, Na, K, Cs, Mg, Zn, Cd or Hg.

In each of these schemes it is possible to use a mixture of reactants that could have different divalent radicals $(\ )_w$ and $(\ )_y$ wherein the number of carbon atoms varies. In addition, $R_1$ and $R_2$ could be bonded to form a cyclic structure to the same metal atom or to adjacent metal atoms.

Another possible synthetic route to suitable polymetallane monomers is to use cyclopolymetallane reactants and (1) subject them to UV radiation, (2) two step reaction with $CH_2=CH(CH_2)_nE$ and then $CH_2=CH(CH_2)_nX$ (wherein n, E and X are the same as identified above), and (3) reacting with $CH_2=CH(CH_2)_nM(X)_2(CH_2)_nCH=CH_2$.

The polymer should have a high amount of metal, at least about 20 weight %, preferably at least about 50 weight %, based on the weight of the polymer. Polymers with such a structure should have very advantageous electrical and thermal conductivity properties and thus can be used in conductive films, fibers and solders and photoresists. In addition, they should be malleable and easy-to-process since they are very soluble in organic solvents and should have good melt processing characteristics.

DETAILED DESCRIPTION OF THE PREFERRED EMBODIMENTS

The first step in our approach to ADMET polymers containing polymetallane segments consists of the design and synthesis of suitable diene monomers containing at least one metal-metal σ bond. In order to determine the compatibility between this functionality and the metathesis catalysts employed in the polymerization, we have concentrated our efforts on the preparation of di- and tristannane dienes. The alkenylation of a tri- or distannane dichloride appeared attractive to us since a variety of carbonated segments can be introduced by the choice of the alkenylating group.

The synthesis of monomer of formula 2 as shown in Scheme 1 below involves the in situ generation of $Bu_2SnHCl$, its dehydrogenative coupling to the distannane dichloride, and the subsequent reaction of this dichloride with a nucleophilic alkenyl group, and we have attempted to reduce this procedure to a one-pot synthesis scheme based on the difficulties often associated with the purification of tin halides.

The room temperature disproportionation of equimolar amounts of $Bu_2SnCl_2$ and $Bu_2SnH_2$ leading to $Bu_2SnHCl$ has been previously reported in Newmann, W. P.; Pedain, J. Tetrahedron 1964, 36, 2461; (b) Kawakami, T.; Suimoto, T.; Shibata, I.; Baba, A.; Matsuda, H.; Sonoda, N. *J. Org. Chem.* 60, 2677 (1995). The equilibrium concentrations are reached in ca. 10 min at 25° C. Addition of a catalytic amount of dry pyridine or a Pd complex to this mixture has also been reported in Newmann et al. to cause the quantitative decomposition of the $Bu_2SnHCl$ to the distannane dichloride. The palladium catalyzed coupling appears to be the most efficient, and $Bu_4SN_2CL_2$ solutions are obtained after—often vigorous—hydrogen evolution from the precursor $Bu_2SnHCl$ solutions. This disappearance of the signal centered at 44.6 ppm and the simultaneous appearance of a new sharp singlet at 109.0 ppm in the (proton decoupled) $^{119}$Sn-NMR ($1J^{119}Sn-^{119}Sn=2420$ Hz), have proven to be very useful in the monitoring of this reaction. We have also observed that this methodology can be extended to other polystannane dichlorides, which can be used as precursors for diene monomers.

The alkenylation of the distannane dichloride is a facile reaction. Gentle reflux of the dichloride with the Grignard reagent generated from 5-bromo-1-pentene affords after workup a mixture of the dienes of formulae 2,3, and 4 identified by their distinct resonances in the $^{119}$Sn-NMR. However, we have been unable to produce 2 free of other dienes, and attempts to separate these dienes have also proven unsuccessful. $Bu_2SnCl_2$ remaining from the incomplete disproportionation reaction accounts for the presence of formula 3, while the coupling of remaining $Bu_2SnH_2$ with $Bu_2SnHCl$ in the second step explains the presence of diene of formula 4. To our surprise, these compounds are quite stable not only to aqueous workup of the Grignard reaction, but also to adsorbents such as silica gel, which allows their isolation in adequate purity for ADMET polymerization.

Upon exposure to the molybdenum catalyst 1, this purified diene mixture produced the ADMET terpolymer of formula 6 in almost quantitative yield. (see Scheme 2 below) Ethylene evolution is very vigorous during the first 4 h of the reaction, and the viscosity of the reaction mixture increases steadily suggesting polymerization. After this time, ethylene bubbling rate decreases, but continues throughout the reaction until viscosity prevents magnetic stirring. Characterization of the crude polymer sample reveals that polymerization has indeed taken place, along with the incorporation of the three stannadienes 2,3 and 4. Both $^{13}C$ and $^{1}H$-NMR of the polymer show the conversion from terminal dienes to internal olefins. New signals at 5.5–5.6 ppm ($^{1}H$), and at 131.2 and 130.6 ppm ($^{13}$C) account for the new olefin linkages, in both cis and trans isomeric forms. Polymerization is also evident by the splitting of the $^{119}$Sn signals originally present in the monomer mixture, due to the slightly different magnetic environments caused by the olefin linkages.

Precipitation of the polymers from CDCl$_3$ or C$_6$D$_6$ solutions into methanol yields the polymers as viscous liquid samples. End group analysis based on NMR Spectroscopy suggests an average degree of polymerization of 20. (Calculated Mn=11,000 g/mol).

EXAMPLE

Mo(CHCMe$_2$Ph)(N-2,6-C$_6$H$_3$—Pr$_2$)(Ocme(CF$_3$)$_2$)$_2$ (catalyst 1) and di-n-butylstannane were synthesized according to, respectively, Schrock, R. R., Murdzek, J. R., Bazan, G. C., DiMare, M., O'Regan, M. *J. Am. Chem. Soc.*, 112, 3875 (1990) and Imori, T., Lu, V., Cai, H., Tilley, T. D., *J. Am. Chem. Soc.*, 117, 9931 (1995), both incorporated herein by reference. 5-Bromo-1-pentene was purchased from Aldrich Chemical Company and distilled from CaH$_2$ immediately before use. Di-n-butyltin dichloride was purchased from Acros Organics and used as received. Diethyl ether was distilled from sodium benzophenone ketyl and stored over 4 Å molecular sieves in an inert atmosphere of argon.

$^1$H (300 MHz), $^{13}$C(75 Mhz), and $^{119}$Sn (112 MHz) NMR was performed on a varian VXR-300 MHz superconducting spectrophotometric system using deuterobenzene (C$_6$D$_6$) as the solvent. $^1$H and $^{13}$C NMR are referenced to an internal 0.05% w/w TMS standard while $^{119}$Sn NMR are referenced to an internal 1% w/w tetramethyltin sample.

Synthesis of 6,6,7,7-tetrabutyl-6,7-distanna-1,11-dodecadiene (formula 2)

In a flame-dried schlenk tube, a solution of 1.24g (4.05 mmol) of Bu$_2$SnCl$_2$ in 6 mL of anhydrous diethyl ether was added via syringe to neat Bu$_2$SnH$_2$, (1.01 g, 4.26 mmol), and this mixture was stirred under an argon atmosphere for 15 min. Dry pyridine (33 μL, 0.40 mmol) was added, and the mixture was stirred for an additional 4 h. The solvent was removed in vacuo and the colorless liquid obtained was weighed and redissolved in 5 mL of diethyl ether to make solution 1.

A suspension of powdered Mg (0.294 g, 12.11 mmol) in diethyl ether (6 mL) was kept in a flame-dried three-neck round bottomed flask under an argon atmosphere. A solution of freshly distilled 5-bromo-1-pentene (1.67 g, 11.18 mmol) in diethyl ether (6 mL) was then slowly added and this mixture was refluxed for 2 h, time after which Solution 1 was slowly dropped using an addition funnel. The resulting mixture was refluxed for 20 h, cooled to room temperature and the supernatant solution was cannula-filtered to a schlenk tube. Addition of pentane (15 mL) and a second cannula filtration afforded a solution which was washed twice with ice-cold 1 M NH$_4$CL (2×15 mL), dried over MgSO$_4$ and filtered through a pad of silica gel. The solvent was removed in vacuo and 1.44 g (64%) of a colorless viscous liquid were obtained. This product (material 5) is a mixture of the three tin containing dienes 6,6-dibutyl-6-stanna-1, 10-undecadiene (material 3), 6,6,7,7-tetrabutyl-6, 7-distanna-1, 11-dodecadiene (material 2), and 6,6,7,7,8,8-hexabutyl-6,7,8-tristanna-1,12-tridecadiene (material 4) in an undetermined ratio. $^1$H NMR: d(ppm)=5.7–5.9 (m, 2 H); 5.0–5.2 (m, 4 H); 2.0–2.2 (m, 4 H); 1.6–1.9 (m); 1.3–1.6 (m); 1.3–1.1 (m); 0.8–1.1 (m). $^{13}$C NMR: d(ppm)=139.2, 115.5, 39.5, 33.9, 31.7, 30.2, 28.9, 28.5, 27.5, 14.5, 11.6–11.3, 10.9–10.6, 9.6–9.3. $^{119}$Sn NMR; d(ppm)=–12.4 (3, C—Sn—C), –76.4 (4, C—Sn—Sn—Sn—C), –83.5 (2, C—Sn—Sn—C), –227.3 (4, C—Sn—Sn—Sn—C). Elemental anal. for C$_{26}$H$_{54}$Sn$_2$ (2). Calcd: C(51.70%), H(9.01%). Found: C(51.67%), H(8.76%). HR-MS for C$_{22}$H$_{45}$Sn$_2$ (2)-C$_4$H$_9$. Calcd: 547.1579 m/z (Average of two analysis).

ADMET Polymerization of mixture of formula 5.

In an argon purged dry box, catalyst 1 (5 mg) was weighed and placed in a 50 mL round bottomed flask adapted with a Rotoflow valve. The monomer mixture (in other words, formula 5) (400 mg) was then added to the flask which was in turn sealed and taken to a high vacuum schlenk line. Ethylene evolution could be evidenced at room temperature during the first 12 h of reaction. After this time, the system was heated to 60° C. and the reaction was continued for 24 h. The reaction was stopped by removal of the heat when magnetic aggitation became impossible or when no further bubbling could be evidenced, and the crude viscous polymeric product of formula 6 was dissolved in C$_6$D$_6$ $^1$H NMR: d(ppm)=5.5–5.6 (b); 2.0–2.4 (b); 1.6–1.9 (m); 1.3–1.6 (m); 1.3–1.1(m); 0.8–1.1 (m). $^{13}$C NMR: d(ppm)= 131.2, 130.6, 38.7, 38.5, 33.9, 31.7, 30.3, 28.9, 28.5, 14.5, 11.6, 112.0, 9.6. $^{119}$Sn NMR: d(ppm)=–11.5, –11.6, –11.8, –75.4, –75.5; –82.6, –82.8, –82.9, –83.0; –226.3, –226.4. Elemental anal. for (C$_6$H$_{50}$Sn$_2$)$_n$. Calcd: C(50.04%), H(8.75%). Found: C(%), H(%).

It should be recognized that the polymeric product of formula 6 is a distribution of polymer chains wherein a portion of the chains will also include a backbone unit that has only one metal atom. However, such polymer chains also will include backbone units with at least two metal atoms as per the invention.

Scheme 1. Synthesis of monomer 2. Alkylation of residual Bu$_2$SnCl$_2$ accounts for the formation of material 3 (m=2 in formula 5 below). The pyridine-catalyzed coupling of Bu$_2$SnH, with Bu$_2$SnHCl in step 3 would yield a tristannane dichloride, a precursor to material 4(m=3 in formula 5 below).

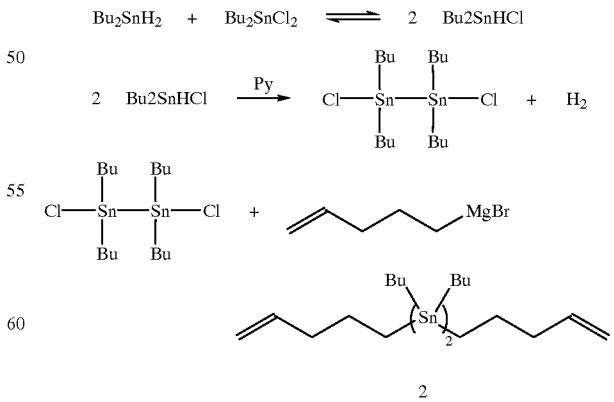

Scheme 2. ADMET polymerization of the monomer mixture 5 to the terpolymer 6.

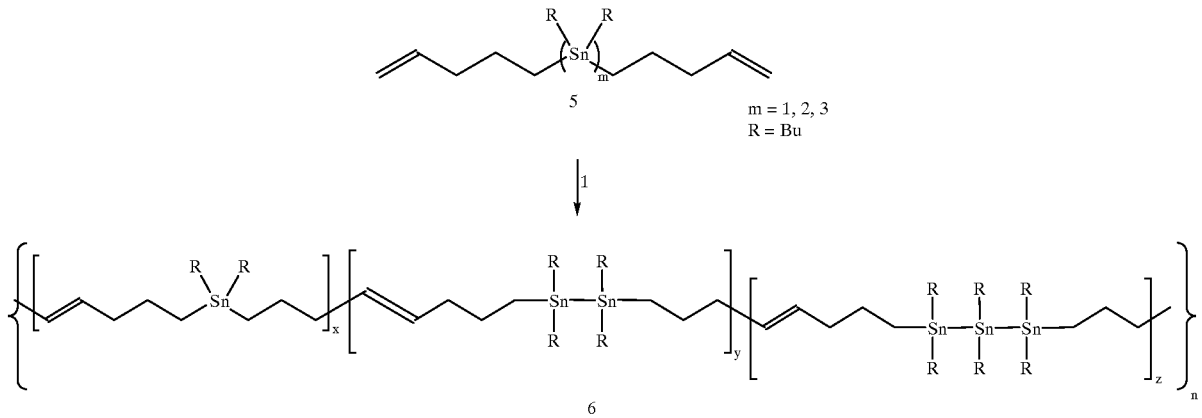

What is claimed is:

1. A polymer having a backbone repeat unit that comprises at least two metal atoms bonded to each other and only one ethylenically unsaturated functional group produced by a cyclic diene metathesis polymerization.

2. A polymer according to claim 1 wherein the metal atoms are selected from a group consisting of Sn, Ge, Pb, Hg, Ni, Pd, Pt, Cr, Fe, Co, Cu and Zn.

3. A polymer according to claim 1 wherein the polymer comprises at least about 20 weight percent metal, based on the weight of the polymer.

4. A polymer according to claim 3 wherein the polymer comprises at least about 50 weight percent metal, based on the weight of the polymer.

5. A polymer according to claim 1 wherein the backbone repeat unit has a structure represented by:

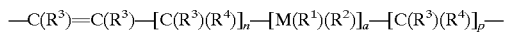

wherein n is 0 to 50; a is at least 2; p is 0 to 50; $R^1$ and $R^2$ are each independently selected from hydrogen, halogen, lower alkyl having 4 or fewer carbon atoms, alkenyl having 4 or fewer carbon atoms, or aromatic having one ring; $R^3$ and $R^4$ are each independently selected from hydrogen and lower alkyl having 1 to 4 carbon atoms; and M is a metal atom selected from a group consisting of Sn, Ge, Pb, Hg, Ni, Pd, Pt, Cr, Fe, Co, Cu and Zn.

6. A polymer according to claim 2 wherein the metal atoms are Sn.

7. A polymer according to claim 5 wherein the metal atoms are Sn.

8. A polymer having a backbone repeat unit that comprises at least two metal atoms bonded to each other and an ethylenically unsaturated functional group separated by at least one saturated carbon atom from the metal-to-metal atoms.

9. A polymer according to claim 5 wherein n and p are each independently 0 to 50.

10. A polymer according to claim 5 wherein n and p are each independently 0 to 4.

* * * * *